US006837118B2

(12) United States Patent
Bonne et al.

(10) Patent No.: US 6,837,118 B2
(45) Date of Patent: *Jan. 4, 2005

(54) HEALTH MONITOR

(75) Inventors: Ulrich Bonne, Hopkins, MN (US); Robert Nickels, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/310,431

(22) Filed: Dec. 5, 2002

(65) Prior Publication Data

US 2004/0107766 A1 Jun. 10, 2004

(51) Int. Cl.[7] ................................................ G01N 1/00
(52) U.S. Cl. ..................................... 73/863.12; 73/23.2
(58) Field of Search ........................ 73/863.11, 863.12, 73/25.01, 23.2, 19.2

(56) References Cited

U.S. PATENT DOCUMENTS

| 4,236,404 | A |   | 12/1980 | Ketchum et al. |           |
|-----------|---|---|---------|----------------|-----------|
| 4,402,211 | A | * | 9/1983  | Sugawara et al.| 73/19.11  |
| 4,502,320 | A | * | 3/1985  | Sakai et al.   | 73/19.1   |
| 4,759,210 | A | * | 7/1988  | Wohltjen       | 73/31.07  |
| 4,944,035 | A |   | 7/1990  | Aagardl et al. |           |
| 5,268,302 | A | * | 12/1993 | Rounbehler et al.| 436/96  |
| 5,591,321 | A | * | 1/1997  | Pyke           | 205/787   |
| 5,898,101 | A | * | 4/1999  | Lyle et al.    | 73/23.2   |
| 5,985,673 | A |   | 11/1999 | Bao et al.     |           |
| 6,041,643 | A | * | 3/2000  | Stokes et al.  | 73/31.06  |
| 6,393,894 | B1| * | 5/2002  | Bonne et al.   | 73/23.2   |
| 6,494,617 | B1| * | 12/2002 | Stokes et al.  | 374/152   |

FOREIGN PATENT DOCUMENTS

WO         0079243 A1    12/2000

OTHER PUBLICATIONS

Goschnick , J., "An electronic nose for intelligent consumer products based on a gas analytical gradient microarray," Microelectronic Engineering, 57–58 pp. 693–704, 2001.

* cited by examiner

Primary Examiner—Michael Cygan
(74) Attorney, Agent, or Firm—Kris T. Fredrick

(57) ABSTRACT

An equipment or environment health monitor having a micro gas apparatus incorporating a phased heater array, concentrator, separator and detector for achieving the sensitivity needed for detection of extremely small amounts of fluids. The apparatus is capable of detecting trace gases, and may be utilized to detect "fault" gas of operating equipment so as to determine, for example, the prospects of imminent failure of the equipment. Also, the micro gas apparatus is capable of detecting miniscule amounts of pollutants in ambient environment of a conditioned or tested space. The output of the apparatus may go to a microcontroller and/or processor for prompt analysis. The output from the microcontroller or processor may go to either a transmitter/receiver for wireless communication or a modem for utility line, cable or optical communication with a station for data and results observation and review.

36 Claims, 12 Drawing Sheets

HEALTH MONITOR

BACKGROUND

The invention pertains to detection, identification and analyses of gases. Particularly, it pertains to the detection of gases that indicate potential problems with equipment or the ambient environment. More particularly, the invention relates to health monitoring of the same.

Aspects of structures and processes related to gas detectors may be disclosed in U.S. Pat. No. 6,393,894, issued May 28, 2002, and entitled "Gas Sensor with Phased Heaters for Increased Sensitivity," which is incorporated herein by reference, and in U.S. Pat. No. 4,944,035, issued Jul. 24, 1990, and entitled "Measurement of Thermal Conductivity and Specific Heat," which is incorporated herein by reference.

The power industry relies on the operation of large, one to ten mega watt (MW) and 15,000 gallon or so oil-immersed electric power distribution transformers, of which there are about 100,000 installed in the United States and about 400,000 in the rest of the world. These transformers cost between one-half and five million dollars and thus amount to an installed base of around 200 billion dollars. Their design lifetime is forty to fifty years; their average life is presently about thirty-five years. The transformers are failing at the rate of about one percent per year. Unexpected failures of the transformers have cost utilities upwards of about eighteen million dollars.

However, it is far too expensive for utilities to replace all this aging equipment at once. So there is great interest in monitoring the "health" of the equipment so that any equipment susceptible to failure can be detected, watched and/or repaired or replaced. The potential multi-million damage, electric service interruption and financial cost resulting from unanticipated failure of utility-power transformers make it necessary to monitor the state of their "health". Such monitoring is being suggested and presently being implemented via labor-intensive periodic off-line or high-capital-cost on-line analysis of the tell-tale changes in the composition and concentration of gases appearing in the transformer oil and in its head-space.

The "fault gases" in the insulating oil or in the head space of the transformer may provide an early indication of transformer failure. Fault gases are produced by high voltage breakdown in oil-filled transformers. Analysis of the dissolved gases in oil or in the head-space of a transformer has shown that they include acetylene ($C_2H_2$), methane ($CH_4$), ethane ($C_2H_6$), carbon monoxide (CO), carbon dioxide ($CO_2$), hydrogen ($H_2$), oxygen ($O_2$) and ethylene ($C_2H_4$). The gas composition is indicative of the type of impending transformer failure and is the reason that low-cost, single gas monitoring does not provide a very high percentage of fault coverage. Detection and analysis of very small amounts of such gases in an inexpensive, efficient and inexpensive manner is desired.

SUMMARY

Multi-gas detection and analysis may be automated via affordable, in-situ, ultra-sensitive, low-power, low-maintenance and compact micro detectors and analyzers, which can wirelessly or by another medium (e.g., wire or optical fiber) send their analysis results to a central or other manned station. A micro gas detector incorporating a phased heater array, concentrator and separator as an enhanced detector contributes to the availability of a low-cost multi-gas analyzer and system to provide equipment health monitoring (EHM) that can increase the probability of detecting equipment failures in time to mitigate the effects of costly downtime and disruption. The micro gas detector was developed as a low-cost approach to sense ozone to meet impending 50 part-per-billion (ppb) maximum emission objectives for electrostatic air cleaners. It is capable of detecting a mixture of trace gases.

This gas detector along with a connective configuration to the equipment and associated microcontroller or processor constitutes a "health monitor" (HM) of the equipment. Monitoring of tell-tale trace gases in utility power transformers is just one of many possible health monitor applications. The critical reliability attribute/expectation is not limited to utility power distribution transformers. Those that provide power to key communication networks as in airports or sustain operation in hospitals or power-sensitive industries (e.g., semiconductor facilities) are also in need for such monitoring. Another application of the health monitor may be the detection and analyses aircraft-cabin air pollutants such as aldehydes, butyric acid, toluene, hexane, and the like, besides the conventional $CO_2$, $H_2O$ and CO. Other monitoring may include conditioned space such as that indoor space of buildings and submarines for levels of gases such as $CO_2$, $H_2O$, aldehydes, hydrocarbons and alcohols, and monitoring outdoor space and/or process streams of processing industries such as in chemical, refining, product purity, food, paper, metal, glass and pharmaceutical industries. Also, health monitoring has a significant place in environmental assurance and protection. It may provide defensive security in and outside of facilities by early detection of chemicals before their concentrations increase and become harmful.

The present health monitor is low-power, fast, compact, low cost, intelligent, wireless or not, low maintenance, robust and highly sensitive. A vast portion of the health monitor may be integrated on a chip with conventional semiconductor processes or micro electromechanical machined system (MEMS) techniques. This kind of fabrication results in low-power consumption, compactness and in situ placement of the monitor. The flow rate of the air or gas sample through the monitor may be very small. Further, a carrier gas for the samples is not needed and thus this lack reduces the dilution of the samples being tested, besides eliminating the associated maintenance and bulk of pressurized gas-tank handling. This approach permits the monitor to provide quick analyses and prompt results, maybe at least an order of magnitude faster than some related art devices. It avoids the delay and costs of labor-intensive laboratory analyses. The monitor is intelligent in that it may have an integrated microcontroller for analysis and determination of gases detected, and may maintain accuracy, successfully operate and communicate information in and from unattended remote locations. The monitor may communicate detector information, analyses and results via utility lines, or optical or wireless media, with the capability of full duplex communication to a host system over a significant distance with "plug-and-play" adaptation and simplicity. The system is net-workable. It is inter-connectable with other gas sample conditioning devices (particle filters, valves, flow and pressure sensors), local maintenance control points, and can provide monitoring via the internet. The monitor is robust. It can maintain accuracy in a high electromagnetic interference (EMI) environment such as in the vicinity of electrical power distribution sub-stations where very strong electrical and magnetic fields are present. The health monitor has high sensitivity. It offers sub-ppm (parts-per-million) level detection which is 100 to 10,000 times better than related art technology, such as conventional gas chromatographs. The monitor is, among other things, a lower-power, faster, and more compact, more sensitive and affordable version of a gas chromatograph.

DESCRIPTION

Figure 1:
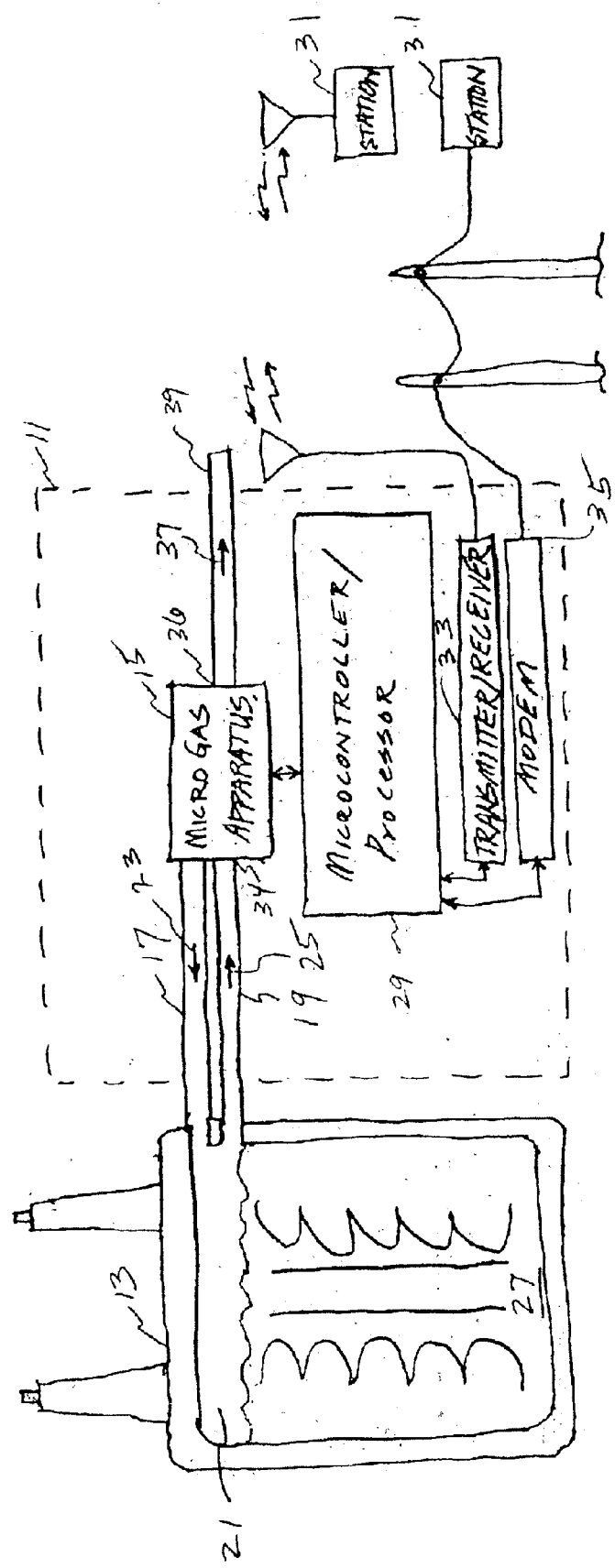
FIG. 1 is an illustration of a health monitor for equipment.
Figure 2:
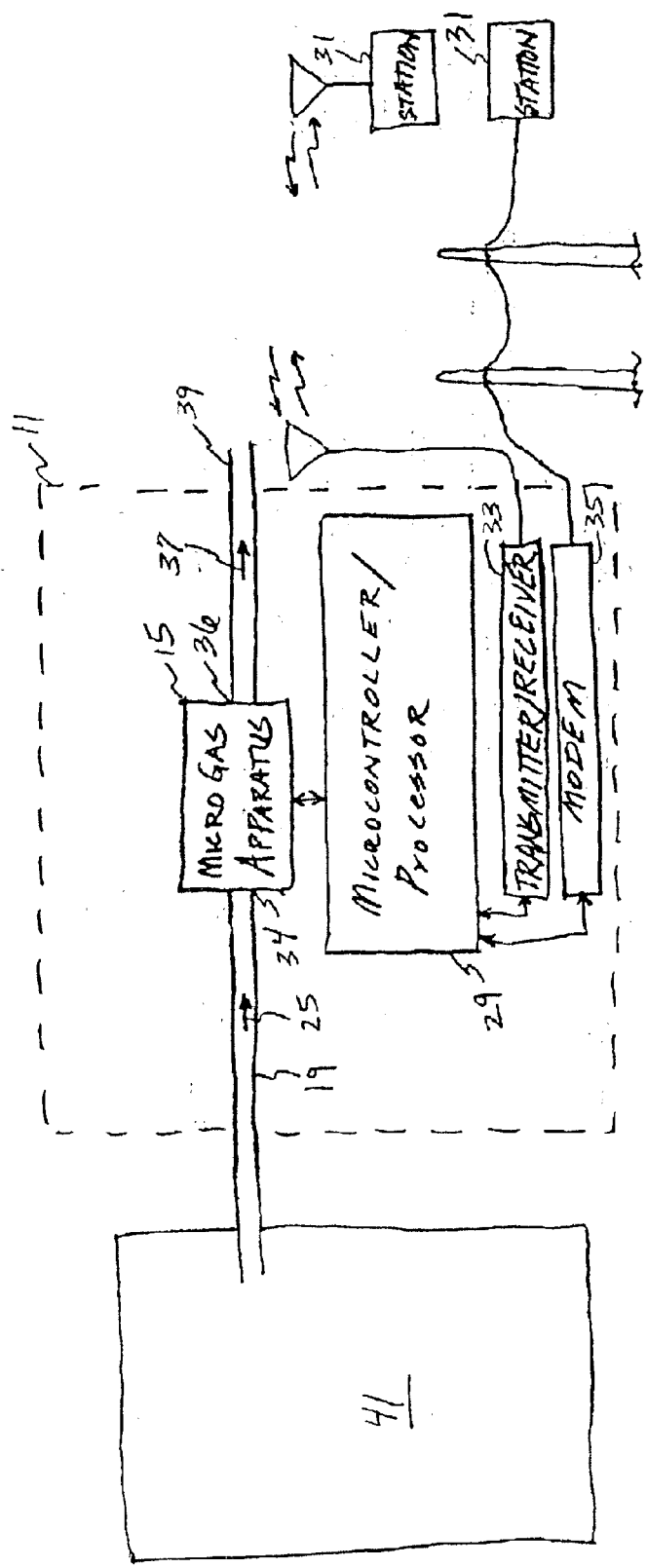
FIG. 2 is an illustration of the health monitor for environmental spaces.
Figure 3:
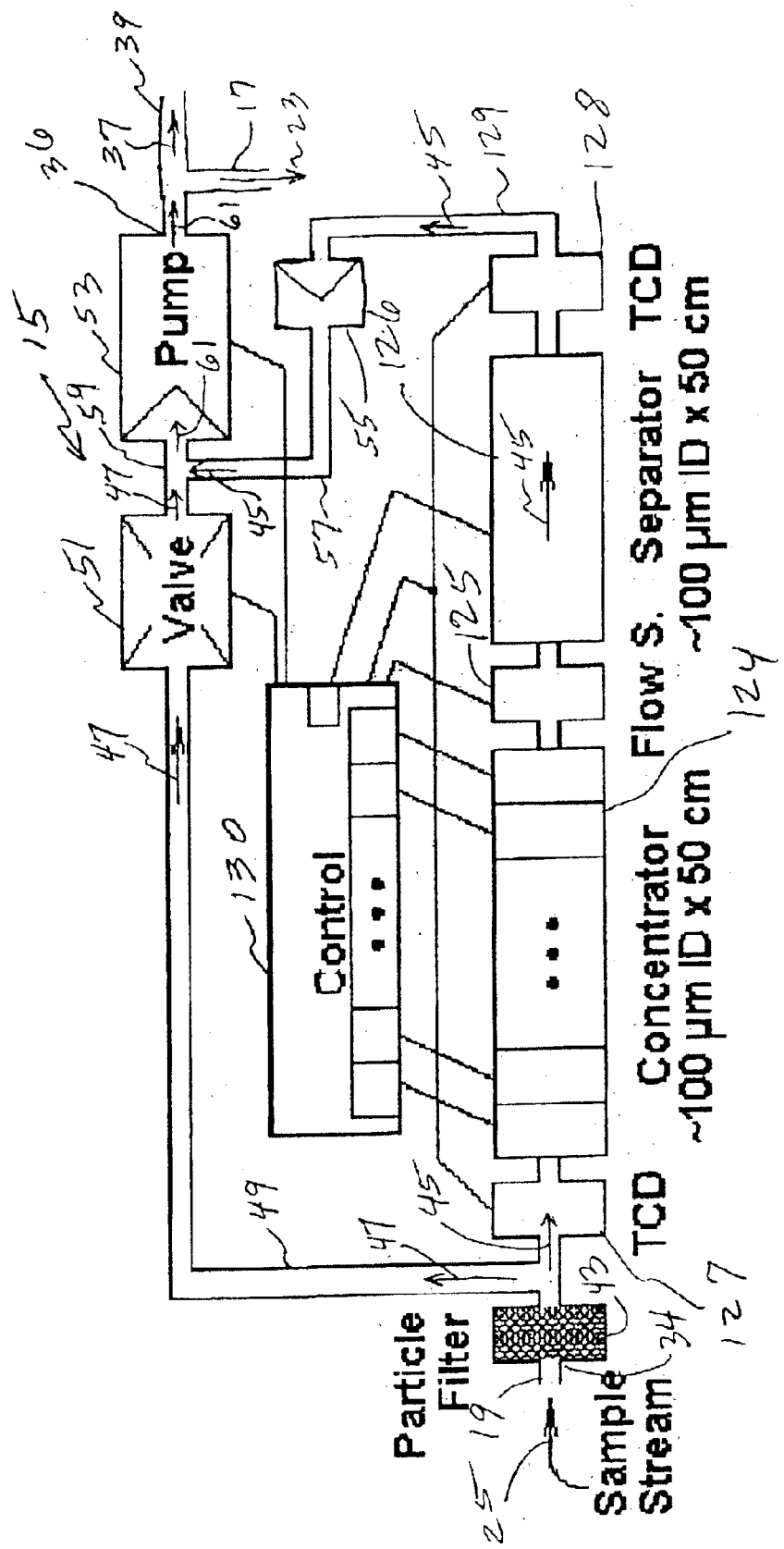
FIG. 3 shows details of a micro gas apparatus.

FIG. 1 reveals a health monitor 11 that may be set up for monitoring the "health" of utility power transformer 13. A micro gas detector apparatus 15 may have two tubes or pipes 17 and 19 connected to a head space 21 of transformer 13. Apparatus 15 may pump a fluid 23 through tube 17 into head space 21. Fluid 23 may displace a fluid 25 in head space 21. Fluid 25 may be "pushed" by displacing fluid 23 through tube 19 to entry port 34 of micro gas apparatus 15. "Fluid" is a generic term that includes liquids and gases as species. For instance, air, gas, water and oil are fluids. In the transformer health monitor, fluid 23 is typically air and fluid 25 may be gas including "fault" gases emanating from insulating oil 27 in transformer 13. Sample stream or gas 25 may be pumped through micro gas detector 15 as shown in FIG. 2. Some excess gas 37 may be discharged via apparatus 15 through tube or pipe 39 from exhaust port 36 as shown in FIGS. 1 and 3. There are certain fault gases that may indicate potential transformer 13 failure. An example is the breakdown of insulation. Such gases may include acetylene, methane, ethane, carbon monoxide, carbon dioxide, hydrogen, oxygen and ethylene. Detection and analysis by monitor 11 may detect, identify and quantify the fluid, i.e., determine the amount of or parts-per-million of the fluid detected. Monitor 11 may be used to detect fluids, monitor the environment around and determine the health of internal and external combustion equipment or mechanisms. An external combustion mechanism may be a space heater, furnace, boiler, or the like. Also, monitor 11 is capable of detecting miniscule amounts of pollutants in ambient environment of a conditioned or tested space. Monitor 11 may indicate the health and the level of toxins-to-people in ambient air. Detectors 127 and 128 results may be sent to microcontroller/processor 29 for analysis, and immediate conclusions and results. This information may be sent on to observer stations 31 for review and further analysis, evaluation, and decisions about the health of transformer 13. Data and control information may be sent from stations 31 to microcontroller/processor 29. Data and information may be sent and received via the wireless medium by a transmitter/receiver 33 at monitor 11 and at stations 31. Or the data and information may be sent and received via wire or optical lines of communication by a modem 35 at monitor 11 and station 31. The data and information may be sent to a SCADA (supervisory control and data acquisition) system. These systems are used in industry to monitor and control plant status and provide logging facilities.

The monitor 11 may be used to detect hazards to people in the environment of or around equipment.

In FIG. 1, transformer 13 may replaced with another kind of equipment such as an electric motor, a generator, an internal combustion engine, air conditioner or other types of equipment. Microcontroller/processor 29 may be programmed to provide a prognosis of the equipment whose health is being monitored in view of the expected fault gases that would be emanated by a certain piece of equipment having potential "health problems."

FIG. 2 reveals health monitor 11 with a hook-up that may be used in a space 41 such as an aircraft-cabin, machinery room, factory, or some place in another environment. The end of input tube or pipe 19 may be in space 41 and exhaust of exit tube 37 may be placed at a distance somewhat removed from space 41. There is no return or air supply tube 17 as in health monitor 11 for equipment in FIG. 1. Monitor 11 for space 41 may itself be within space 41 except that tube 39 may exit space 41.

FIG. 3 reveals certain details of micro gas apparatus 15. Further details and variants of it are described below in conjunction with subsequent figures. Sample stream 25 may enter input port 34 from pipe or tube 19. There may be a particle filter 43 for removing dirt and other particles from the stream of fluid 25 that is to enter apparatus 15. This removal is for the protection of the apparatus and the filtering should not reduce the apparatus' ability to accurately analyze the composition of fluid 25. Dirty fluid (with suspended solid or liquid non-volatile particles) could possibly impair proper sensor function. A portion 45 of fluid 25 flows through a thermal-conductivity detector 127 and a portion 47 of fluid 25 flows through tube 49 to a one-way valve 51. Pump 53 causes fluid 47 to flow from the output of particle filter 43 through tube 49 and valve 51. Modulating valve 51 controls the flow through the sensor via tube 45 by adjusting the suction pressure of pump 55 in tube 129. Pump 55 causes fluid 45 to flow from the output of filter 43 through detector 127, concentrator 124, flow sensor 125, separator 126, thermal-conductivity detector 128 and tube 129. Pump 55 pumps the fluid through tube 57 to tube 59 where it joins fluid 47 as a combined fluid 61. Fluid 61 is pumped to output port 36 by pump 53. Fluid 61 may split into two streams 23 and 37 which flow through tubes or pipes 17 and 39, respectively. Data from detectors 127 and 128 may be sent to control 130, which in turn relays data to microcontroller and/or processor 29 for processing. Resultant information may be sent to station 11.

Figure 4:
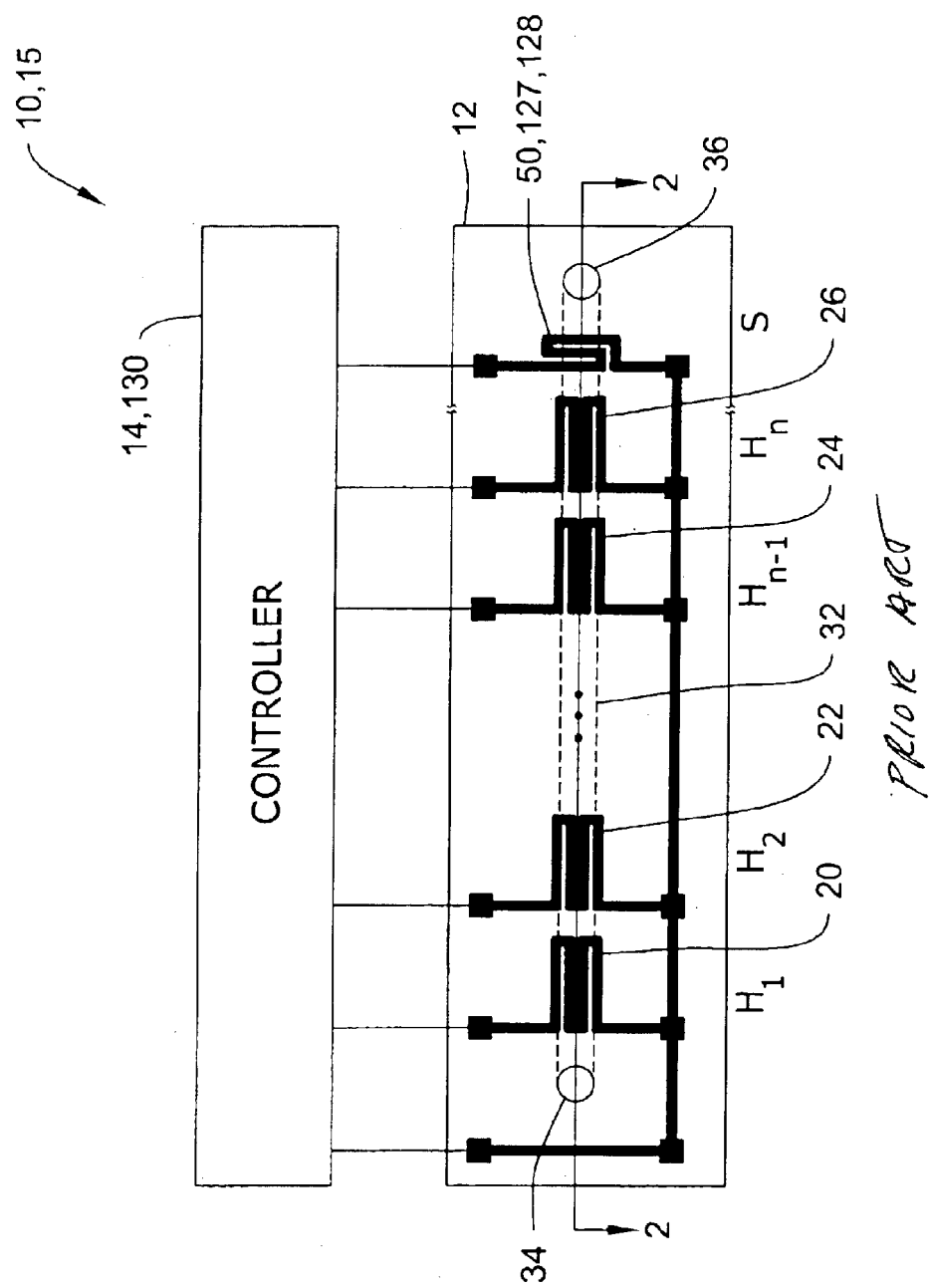
FIG. 4 is a layout of an illustrative sensor apparatus.
Figure 5:
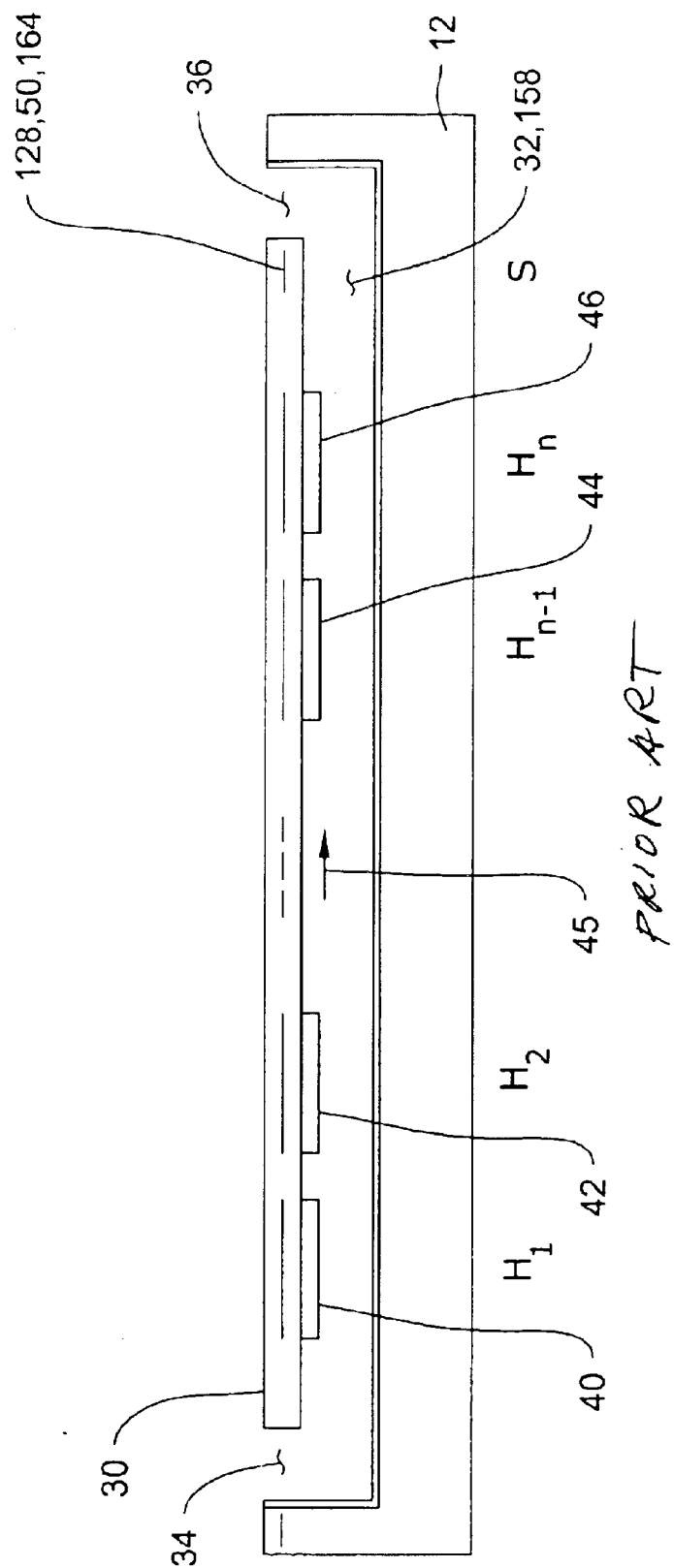
FIG. 5 is a cross-sectional view taken along line 2—2 of FIG. 4.

FIG. 4 is a schematic diagram of part of the sensor apparatus 10 or 15. The sensor apparatus may include a substrate 12 and a controller 14. Controller 14 may or may not be incorporated into substrate 12. Substrate 12 may have a number of thin film heater elements 20, 22, 24, and 26 positioned thereon. While only four heater elements are shown, any number of heater e elements may be provided, for instance, between two and one thousand, but typically in the 20–100 range. Heater elements 20, 22, 24, and 26 may be fabricated of any suitable electrical conductor, stable metal, or alloy film, such as a nickel-iron alloy sometimes referred to as permalloy, with a composition of eighty percent nickel and twenty percent iron; platinum, platinum silicide, and polysilicon. Heater elements 20, 22, 24, and 26 may be provided on a thin, low-thermal mass, low-in-plane thermal conduction, support member 30, as shown in FIG. 5.

Substrate 12 also has a well-defined channel 32 for receiving the sample fluid stream 45. Channel 32 may be fabricated by selectively etching silicon substrate 12 beneath support member 30. The channel includes an entry port 34 and an exhaust port 36.

The sensor apparatus may also include a number of interactive elements inside channel 32 so that they are exposed to the sample fluid stream 45. Each of the interactive elements may be positioned adjacent, i.e., for closest possible contact, to a corresponding heater element. For example, and referring, to FIG. 5, interactive elements 40, 42, 44, and 46 may be provided on the lower surface of support member 30, and adjacent to heater elements 20, 22, 24, and 26, respectively. The interactive elements may be formed from any number of films commonly used in liquid or gas chromatography, such as silica gel or active carbon.

Interactive elements may be formed by passing, a stream of material carrying the desired sorbent material through channel 32. This provides an interactive layer throughout the channel. If separate interactive elements are desired, the coating may be selectively "developed" by providing a temperature change to the coating, via the heater elements. After the coating is developed, a stream of solvents may be provided through channel 32 to remove the coating everywhere except where the coating has been developed, leaving only the sorbent material that is adjacent the heater elements.

Controller 14 or 130 may be electrically connected to each of the heater elements 20, 22, 24, 26, and detector 50 as shown in FIG. 4. Controller 14 or 103 may energize heater elements 20, 22, 24, and 26 in a time phased sequence (see bottom of FIG. 6) such that each of the corresponding interactive elements 40, 42, 44, and 46 become heated and desorb selected constituents into a sample fluid stream 45 at precisely the time when an upstream concentration pulse, produced by one or more upstream interactive elements, reaches the interactive element. Any number of interactive elements may be used to achieve the desired concentration of constituent gases in the concentration pulse. The resulting concentration pulse may be provided to detector 50, 128, 164 for detection and analysis. Detector 50, 127, 128 or 164 may be a thermal conductivity detector, discharge ionization detector, or any other type of detector such as that typically used in gas or fluid chromatography.

Figure 6:
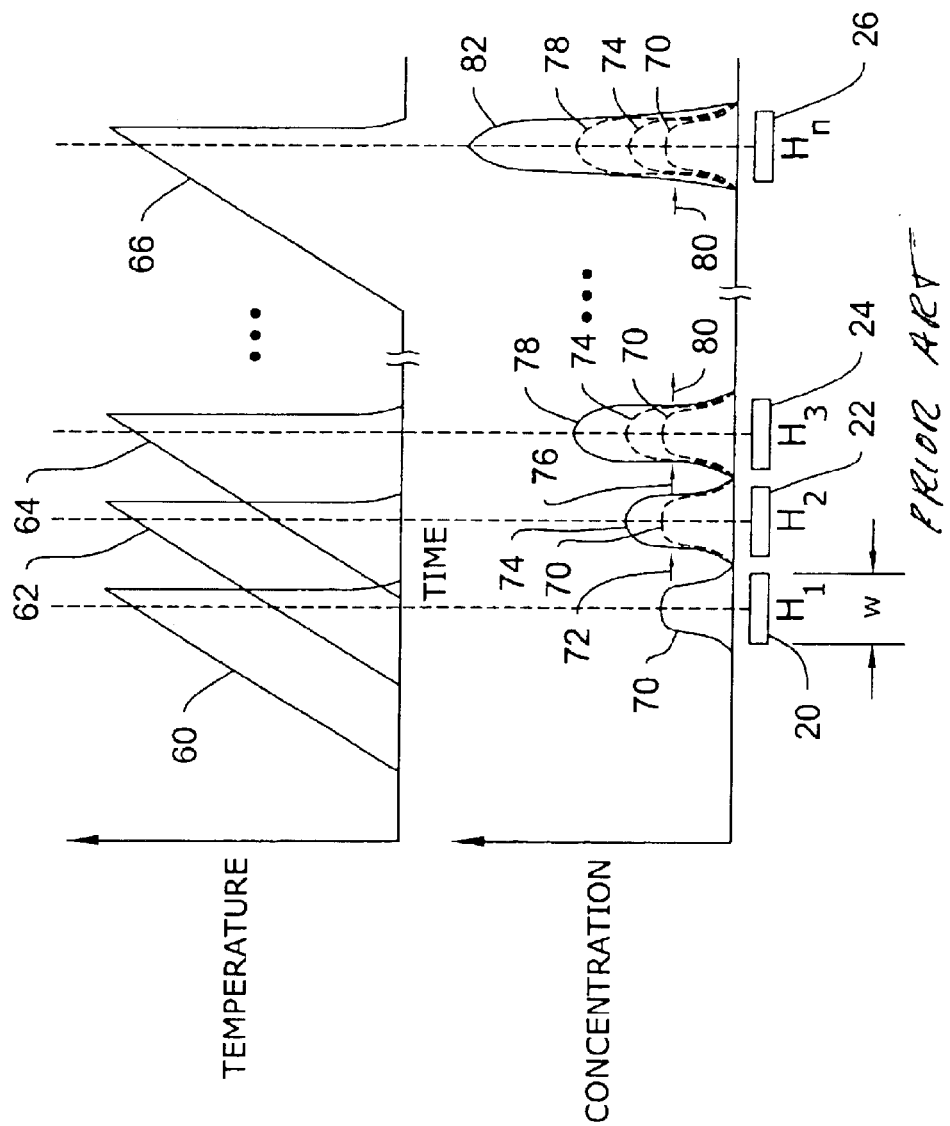
FIG. 6 is a graph showing illustrative heater temperatures, along with corresponding concentration pulses produced at each heater element of the sensor apparatus.

FIG. 6 is a graph showing illustrative heater temperatures, along with corresponding concentration pulses produced at each heater element. As indicated above, controller 14 or 130 may energize heater elements 20, 22, 24, and 26 in a time phased sequence. Illustrative time phased heater temperatures for heater elements 20, 22, 24, and 26 are shown by temperature profiles or lines 60, 62, 64, and 66, respectively.

In the example shown, the controller 14, 130 (FIG. 4) may first energize first heater element 20 to increase its temperature as shown at line 60. Since first heater element 20 is thermally coupled to first interactive element 40, the first interactive element desorbs selected constituents into the sample fluid stream 45 to produce a first concentration pulse 70 at the detector 128 or 50 or 164, if no other heater elements were to be pulsed. The sample fluid stream carries the first concentration pulse 70 downstream toward second heater element 22, as shown by arrow 72.

Controller 14 (or 130) may next energize second heater element 22 to increase its temperature as shown at line 62. Since second heater element 22 is thermally coupled to second interactive element 42, the second interactive element also desorbs selected constituents into sample fluid stream 45 to produce a second concentration pulse. Controller 14, 130 may energize second heater element 22 such that the second concentration pulse substantially overlaps first concentration pulse 70 to produce a higher concentration pulse 74, as shown in FIG. 6. The sample fluid stream carries larger concentration pulse 74 downstream toward third heater element 24, as shown by arrow 76.

Controller 14, 130 may then energize third heater element 24 to increase its temperature as shown at line 64 in FIG. 6. Since third heater element 24 is thermally coupled to third interactive element 44, third interactive element 44 may desorb selected constituents into the sample fluid stream to produce a third concentration pulse. Controller 14, 130 may energize third heater element 24 such that the third concentration pulse substantially overlaps larger concentration pulse 74 provided by first and second heater elements 20 and 22 to produce an even larger concentration pulse 78. The sample fluid stream carries this larger concentration pulse 78 downstream toward an "Nth" heater element 26, as shown by arrow 80.

Controller 14, 130 may then energize "Nth" heater element 26 to increase its temperature as shown at line 66. Since "Nth" heater element 26 is thermally coupled to an "N-th" interactive element 46, "N-th" interactive element 46 may desorb selected constituents into sample fluid stream 45 to produce an "N-th" concentration pulse. Controller 14, 130 may energize "N-th" heater element 26 such that the "N-th" concentration pulse substantially overlaps larger concentration pulse 78 provided by the previous N-1 interactive elements. The sample fluid stream carries "N-th" concentration pulse 82 to either a separator 126 or a detector 50, 128 or 164, as described below.

As indicated above, heater elements 20, 22, 24, and 26 may have a common length. As such, controller 14, 130 can achieve equal temperatures of the heater elements by providing an equal voltage, current, or power pulse to each heater element. The voltage, current, or power pulse may have any desired shape including a triangular shape, a square shape, a bell shape, or any other shape. An approximately square shaped voltage, current, or power pulse is used to achieve temperature profiles 60, 62, 64, and 66 shown in FIG. 6.

Figure 7:
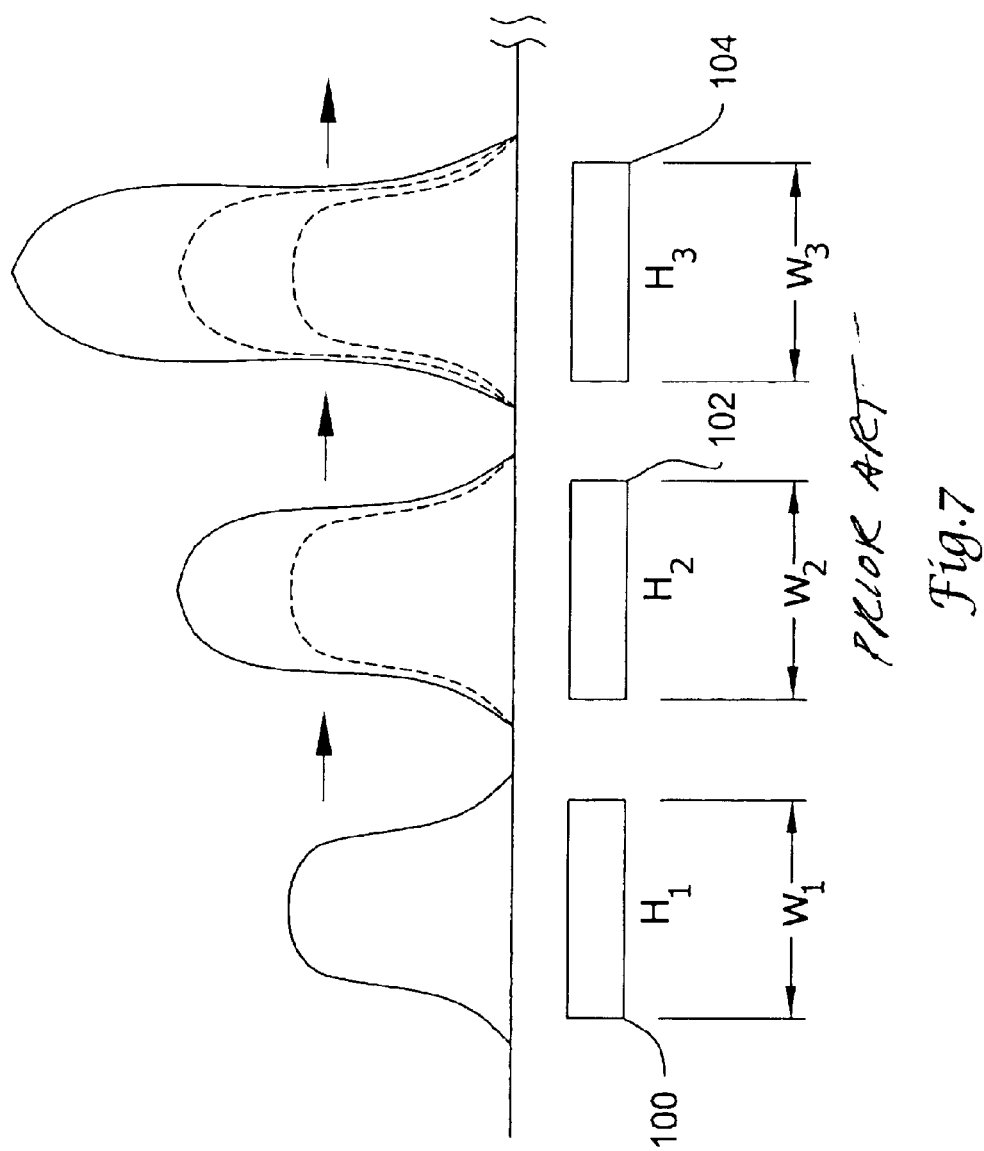
FIG. 7 is a graph showing a number of heater elements having lengths to match the expected increased lengths of the concentration pulses due to diffusion.

FIG. 7 is a graph showing a number of heater elements having lengths to match the expected increased length of the concentration pulses due to diffusion. It is recognized that each of the concentration pulses may tend to reduce in amplitude and increase in length when traveling down channel 32 due to diffusion. To accommodate this increased length, it is contemplated that the length of each successive heater element may be increased along the sample fluid stream. For example, a second heater element 102 may have a length $W_2$ that is larger than a length $W_1$ of a first heater element 100. Likewise, a third heater element 104 may have a length $W_3$ that is larger than length $W_2$ of second heater element 102. Thus, it is contemplated that the length of each heater element 100, 102, and 104 may be increased, relative to the adjacent upstream heater element, by an amount that corresponds to the expected increased length of the concentration pulse of the upstream heater elements due to diffusion.

To simplify the control of the heater elements, the length of each successive heater element may be kept constant to produce the same overall heater resistance between heater elements, thereby allowing equal voltage, current, or power pulses to be used to produce similar temperature profiles. Alternatively, the heater elements may have different lengths, and the controller may provide different voltage, current, or power pulse amplitudes to the heater element to produce a similar temperature profile.

Figure 8:
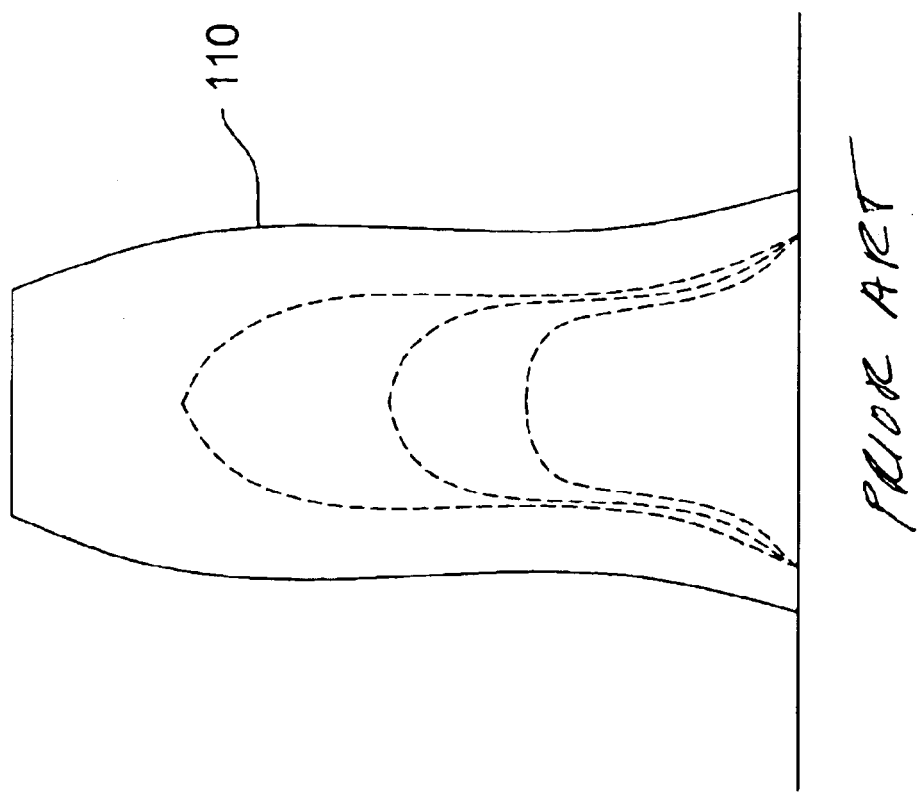
FIG. 8 is a graph showing a concentration pulse that reaches a 100 percent concentration level.

FIG. 8 is a graph showing a concentration pulse 110 that achieves a 100 percent concentration level. It is recognized that even though concentration pulse 110 has achieved a predetermined concentration threshold, such as 100 percent, the concentration of the corresponding constituent can still be determined. To do so, detector 50, 128, 164 may detect the concentration pulse 110, and controller 14, 130 may integrate the output signal of the detector over time to determine the concentration of the corresponding constituent in the original sample of stream 45.

Figure 9:
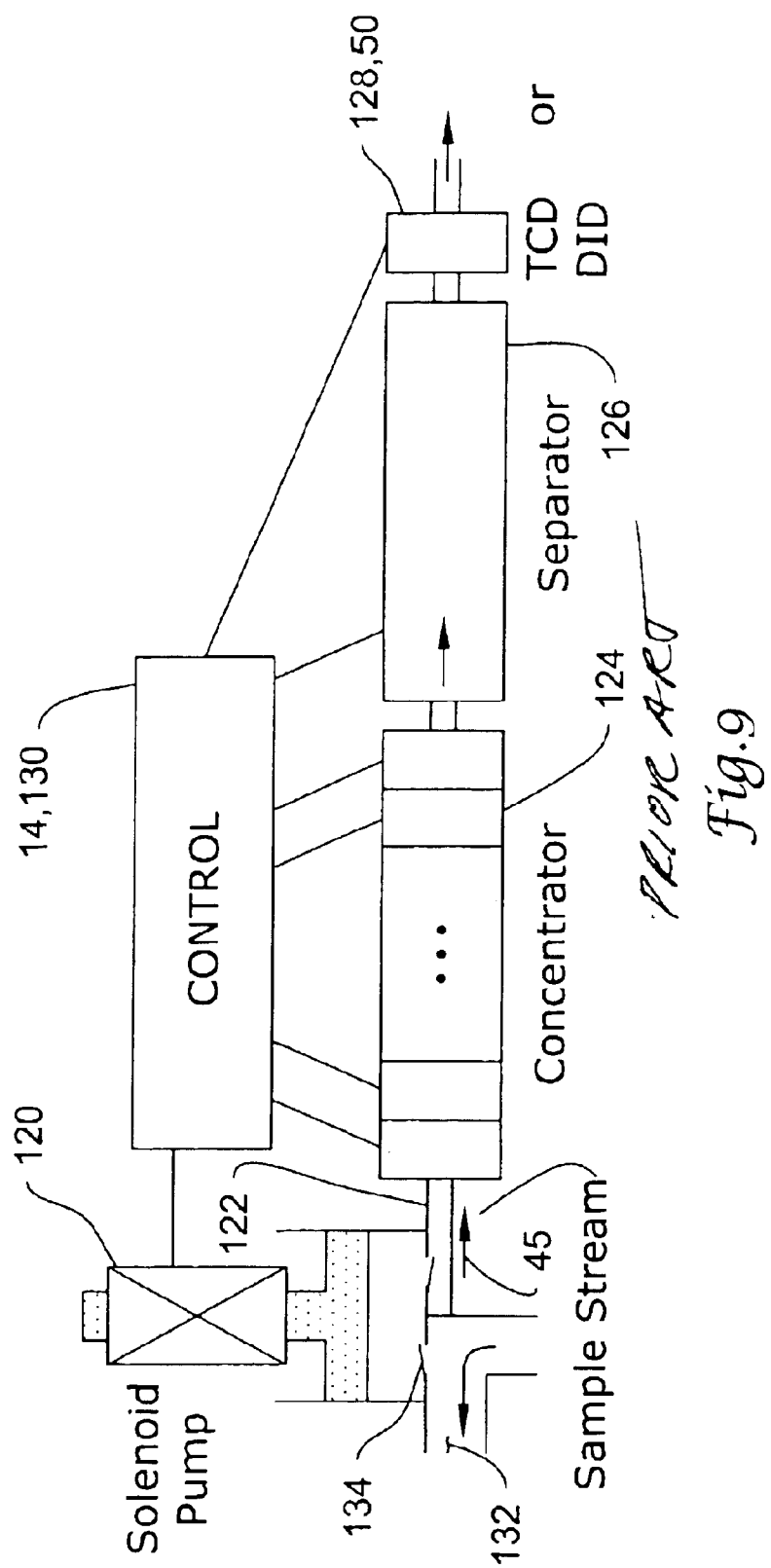
FIG. 9 is a layout of another illustrative sensor assembly.

FIG. 9 is a schematic view of another illustrative sensor assembly 15 similar to that of FIG. 3. The sensor assembly may include a solenoid pump 120, a sample fluid stream 122, a concentrator 124, a separator 126, a detector 128, and a controller 14 or 130. At the request of the controller 14, 130, solenoid pump 120 may draw a sample 45 from a flue gas stream 132 through a one-way valve 134. Controller 14, 130 may then direct solenoid pump 120 to provide sample fluid stream 45, at a desired pressure, to concentrator 124.

Concentrator 124 may include two or more interactive elements that are in communication with sample fluid stream 45. Concentrator 124 also may include two or more heater elements that are in thermal communication with the interactive elements. When energized, each heater element heats a corresponding interactive element, causing the interactive element to desorb selected constituents into the sample fluid stream. As described above, controller 14, 130 may energize the heater elements in a time phased sequence to provide an increased concentration pulse.

Sample fluid stream 45 may carry the concentration pulse to separator 126. Separator 126 may separate selected constituents of the concentration pulse and provide the separated constituents to detector 50, 128, 164. This detector may provide a signal to controller 14, 130 indicating the concentration level of each constituent. Controller 14, 130 may determine the actual concentration level of each constituent in the original gas sample by dividing the sensed concentration level by the concentration amplification provided by the sorbent material of each interactive element and the multiplier effect provided by the phased heater arrangement.

Figure 10:
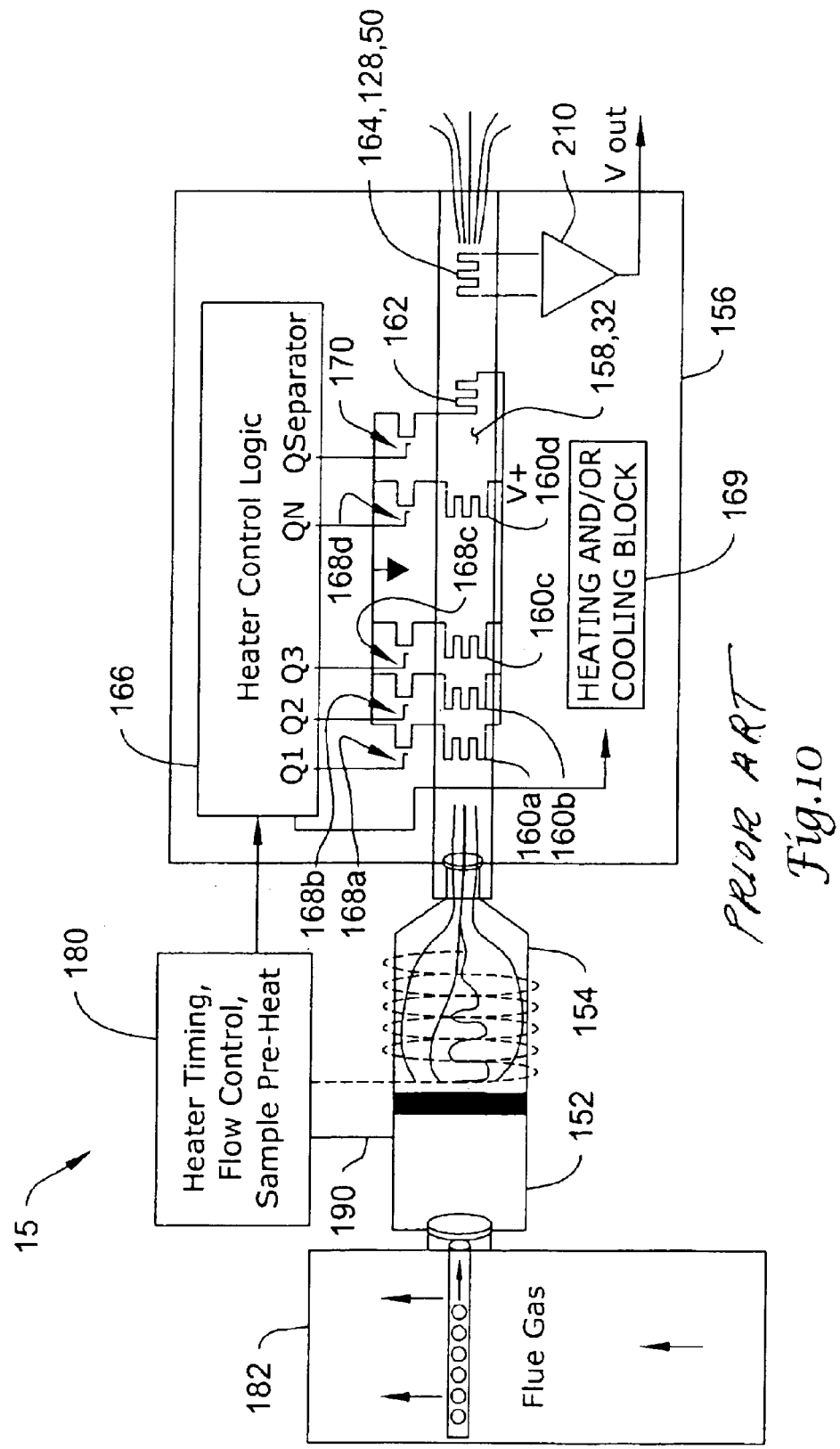
FIG. 10 is a schematic view of a version the sensor assembly.
Figure 11:
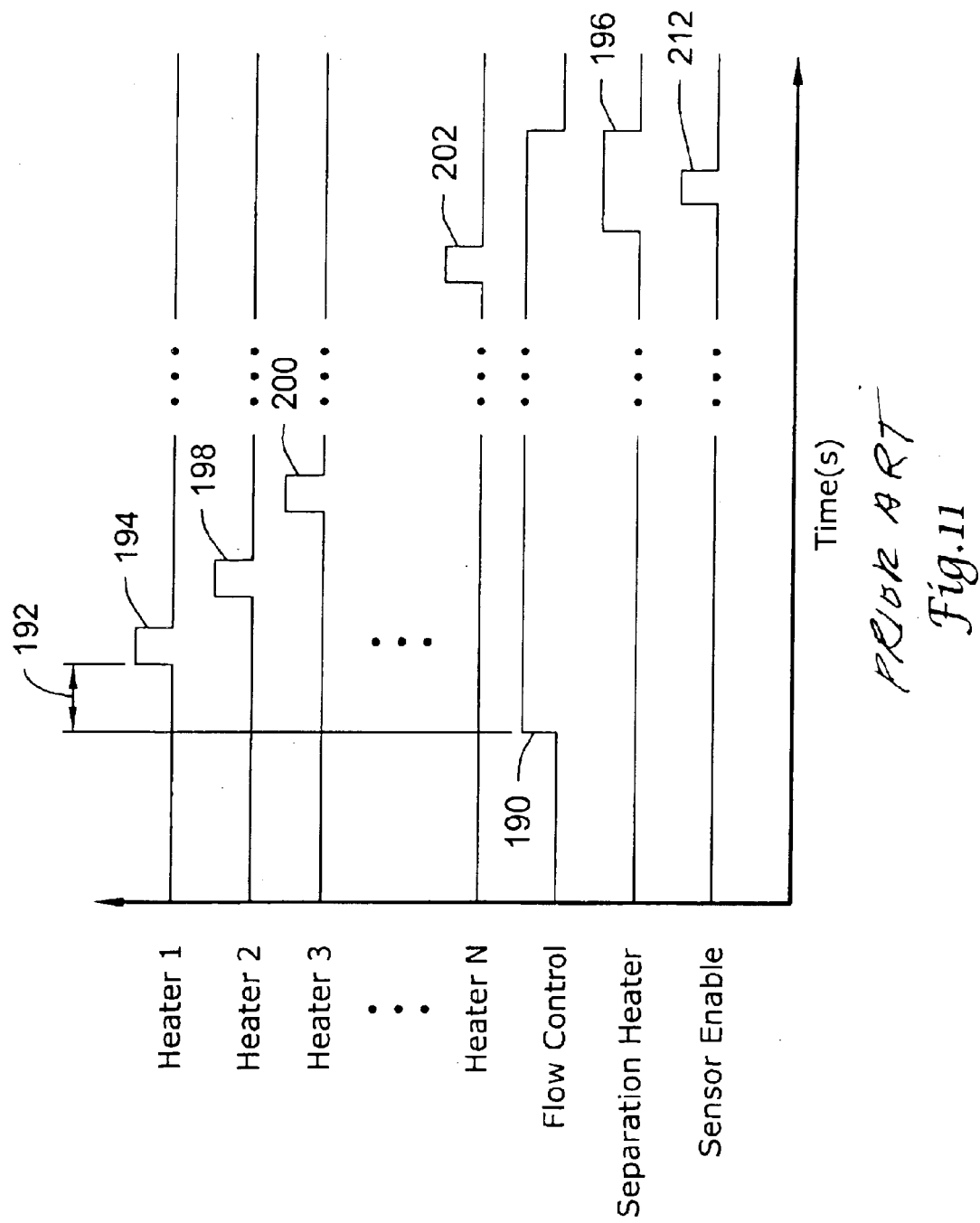
FIG. 11 is a timing chart showing the operation of the sensor assembly of FIG. 10.

FIG. 10 is a schematic view of another illustrative sensor assembly 15. FIG. 11 is a timing chart showing the operation of sensor assembly 15 of FIG. 10. Sensor assembly 15 may include a pump 152, a gas preheater 154, and a microbridge type integrated circuit chip 156. The microbridge type integrated circuit includes a channel 158, 32, a number of heater elements 160a, 160b, 160c, and 160d, a separation heater 162, and a detector 164, 128, 50. Each of heater elements 160a, 160b, 160c, and 160d, separation heater 162, and detector 164 are provided on a support member 30 that extends over the channel 158, 32 (e.g., FIG. 5). Interactive elements (not explicitly shown) are placed in channel 158, 32 and in thermal communication with each of heater elements 160a, 160b, 160c, and 160d.

Microbridge type integrated circuit chip 156 also may include a heater control block 166 and a number of energizing transistors 168a, 168b, 168c, 168d, and 170. Heater control block 166 can individually energize each of heater elements 160a, 160b, 160c, and 160d, by activating a corresponding energizing transistor 168a, 168b, 168c, 168d, respectively. Likewise, heater control block 166 can energize separation heater 162 by turning on transistor 170. Heating or cooling block 169 (of FIG. 10) complements preheater 154 in maintaining an average or overall temperature that is optimal for operation of sensor assembly 15.

A sensor assembly control block 180 directs the overall operation of sensor assembly 15. Sensor assembly control block 180 first asserts a flow control signal 190 to pump 152. Flow control signal 190 is shown in FIG. 11. In response, pump 152 draws a sample from flue 182 and provides the sample, at a desired pressure, to preheater 154 and eventually to channel 158, 32. Preheater 154 preheats and the heater maintains the sample gas at optimal operating element temperature and thus helps to prevent loss of sample due to condensation and to increase the amount of constituents that can be accumulated in each of the interactive elements.

The sample fluid stream passes down channel 158, 32 for a predetermined time period 192 until the interactive elements reach a state of substantially saturation of adsorption of one or more constituents from the sample fluid stream and reach equilibrium. Thereafter, sensor assembly control block 180 notifies heater control block 166 to begin heating the heater elements in a time phased sequence. Heater control block 166 first provides a first heater enable signal 194 and a separation heater enable signal 196, as shown in FIG. 11. First heater enable signal 194 turns on transistor 168a, and separation heater enable signal 196 turns on transistor 170. Transistor 168a provides current to first heater element 160a, causing first heater element 160a to increase in temperature. This heats the corresponding interactive element, which desorbs one or more constituents into the sample fluid stream in the form of a first concentration pulse. The first concentration pulse is carried downstream toward second heater element 160b by the sample fluid stream. This process is repeated for the 3rd, 4th and N-th elements.

Heater control block 166 then provides a second heater enable signal 198, which turns on transistor 168b. Transistor 168b provides current to second heater element 160b, causing second heater element 160b to increase in temperature. This heats the corresponding interactive element, which desorbs one or more constituents into the sample fluid stream in the form of a second concentration pulse. Heater control block 166 may time second heater enable signal 198 such that the second concentration pulse substantially overlaps the first concentration pulse. Both the first and second concentration pulses are carried downstream toward third heater element 160c.

The timing of second heater enable signal 198 relative to first heater enable signal 194 may be established by prior calibration. However, the heater control block 166 may sense the resistance of second heater element 160b. It is recognized that the resistance of second heater element 160b will begin to change when the first concentration pulse arrives at second heater element 160b because the first concentration pulse is typically hotter than the sample fluid stream. Once a predetermined resistance change is sensed in second heater element 160b, heater control block 166 may energize second heater element 160b via transistor 168b. The remaining heater enable signals may be likewise controlled.

Heater control block 166 may then provide a third heater enable signal 200, which turns on transistor 168c. Transistor 168c provides current to third heater element 160c, causing third heater element 160c to increase in temperature. This heats the corresponding interactive element, which desorbs one or more constituents into the sample fluid stream in the front of a third concentration pulse. Heater control block 166 may time third heater enable signal 200 such that the third concentration pulse substantially overlaps the first and second concentration pulses. The first, second, and third substantially overlapping concentration pulses are carried downstream toward "Nth" heater element 160d.

Heater control block 166 may then provide an "Nth" heater enable signal 202, which turns on transistors 168c. Transistor 168c provides current to "Nth" heater element 160d, causing "Nth" heater element 160d to increase in temperature. This heats the corresponding interactive element, which desorbs one or more constituents into the sample fluid stream in the form of an "Nth" concentration pulse. The heater control block 166 may time "Nth" heater enable signal 202 such that the "Nth" concentration pulse substantially overlaps the previously generated concentration pulses. The resulting concentration pulse is carried downstream to separator heater 162. Separator heater 162, in conjunction with the channel 158, may separate selected constituents in the concentration pulse into individual constituent components. The separator's temperature ramp should not start before the end of the Nth pulse to the N-th concentrator element. Thus, pulse 196 begins after pulse 202 ends, as shown in FIG. 11. The individual constituent components may include one or more compounds, depending on a number of factors including the sample gas provided.

Transistor 170 then energizes separation heater 162 at the beginning of pulse 196 in FIG. 11 resulting in the heater 162 temperature having an increasing amplitude from room temperature up to about 200 degrees C. (or other temperature of design) versus time up to about one-half of the length of pulse 196 and then to remain at that temperature for the remaining time of pulse 196. Heater 162 separates the various constituents into individual components, as described above. The separated constituents are carried downstream to detector 164 by the sample fluid stream. Detector 164 may be a thermal conductivity detector, discharge ionization detector, or any other type of detector such as those commonly used in gas chromatography. Detector 164 may sense the concentration levels of each individual constituent component, and provides a corresponding signal to amplifier 210. Amplifier 210 may amplify the detector output signal and provide the detector output signal to a data processing unit for analysis. Heater control block 166 may provide a detector enable signal 212 to enable the detector only when the individual constituent components are present.

Figure 12:
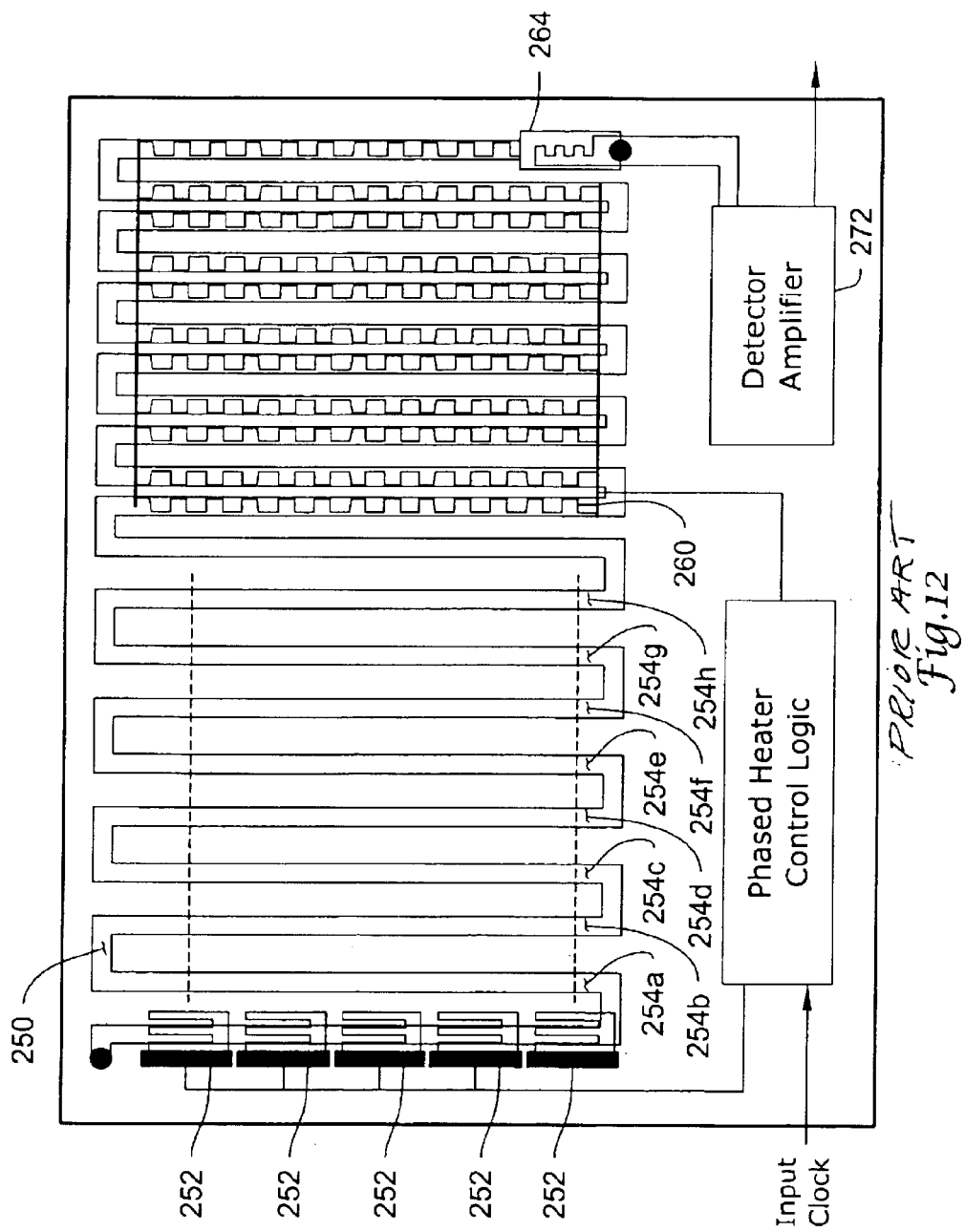
FIG. 12 is a basic layout of an integrated circuit that includes a concentrator, a separator, and a sensor.

FIG. 12 is a basic layout of an integrated circuit that includes a concentrator, a separator, and a detector of micro gas apparatus 15. The integrated circuit may include a channel 250 that traverses back and forth across the chip as shown in FIG. 13. A first part of channel 250 has a number of heater elements 252 extending thereover on a support member, like support member 30 as described above. Interactive elements (not explicitly shown) are positioned in channel 250 adjacent each of the heater elements. While only one column of heater elements 252 is shown, it is contemplated that each of the channel legs 254a-h may have a column of heater elements 252. There may be between one two hundred and one thousand heater elements spaced along channel 250.

A second downstream portion of channel 250 has a separation heater 260 extending thereover. The separation heater helps separate the various constituents in the concentration pulses provided by the heater elements 252. Finally, a detector 264 is provided over the channel 250 downstream of the separation heater 260. The detector may sense the concentration of each of the separated constituent components provided by the separator.

Because the concentrator, separator, and detector are provided on an integrated circuit, other conventional electronic circuits can be easily integrated therewith. A phased heater control block 270 and amplifier 272 may be fabricated on the same substrate. Chemical sensors, especially chemical microsensors as described, potentially afford many attractive features such as low cost, high sensitivity, ruggedness, and very small size.

Although the invention has been described with respect to at least one illustrative embodiment, many variations and modifications will become apparent to those skilled in the art upon reading the present specification. It is therefore the intention that the appended claims be interpreted as broadly as possible in view of the prior art to include all such variations and modifications.

What is claimed is:

1. A health monitoring system comprising;
    a micro gas detector connected to an equipment so as to detect a gas from the equipment; and
    a processor connected to said micro gas detector; and wherein:
    said micro gas detector comprises heaters along a channel, and
    the heaters are structured so as to turn on sequentially to provide a heat pulse that increases as it moves through the channel.

2. The system of claim 1, wherein the at least two interactive elements have an interactive substance that can absorb and desorb constituents of a fluid from the equipment.

3. The system of claim 1, wherein said processor may identify the gas detected by said micro gas detector.

4. The system of claim 3, wherein detection and identification of the gas by said micro gas detector and processor, respectively, may indicate a health of the equipment.

5. The system of claim 3, wherein detection and identification of the gas by said micro gas detector and processor, respectively, may indicate a hazard to people in or around the equipment.

6. The system of claim 4, wherein the health of the equipment may indicate a probability of failure of the equipment.

7. The system of claim 6, wherein the micro gas detector may do less than one part per million detection of the gas.

8. The system of claim 7, further comprising:
    a modem connected to said processor; and
    a communication device connected to said processor for sending information from said processor to a remote station.

9. The system of claim 8, wherein the equipment is an electrical power transformer.

10. The system of claim 9, wherein the gas may be of a group including fault gases such as acetylene, methane, ethane, carbon monoxide, carbon dioxide, hydrogen, oxygen and ethylene.

11. The system of claim 8, wherein the equipment is an electrical motor.

12. The system of claim 8, wherein the equipment is an air conditioner.

13. The system of claim 8, wherein the equipment is an internal combustion mechanism.

14. The system of claim 8, wherein the equipment is an air processing system for monitoring the presence of at least one gas.

15. The system of claim 8 wherein the equipment is an air processing system for monitoring the presence of at least one gas in an enclosure for people.

16. The system of claim 14, wherein the at least one gas is of a group including pollutants such as aldehydes, butyric acid, toluene, hexane, carbon monoxide, carbon dioxide and water vapor.

17. The system of claim 1, further comprising a separator connected downstream to the channel, to separate constituents from a fluid from the equipment.

18. A means for monitoring the health of equipment comprising:
    means for detecting a gas in a fluid from the equipment comprising phased heaters that turn on sequentially through a channel for creating an increasing pulse of heat in the fluid as it moves through the channel for concentrating the fluid in a channel from the equipment; and
    means for processing, connected to said means for detecting a gas, for identifying the gas.

19. The means of claim 18, wherein said means for processing may quantify the gas.

20. The means of claim 18, wherein detection and identification of the gas by said means for detecting and means for identifying, respectively, may indicate a health of the equipment.

21. The means of claim 20, wherein the health of the equipment may indicate a probability of a failure of the equipment.

22. The means of claim 21, further comprising means for sending information from said means for processing to a remote station.

23. The means of claim 22, wherein said means for detecting a gas may do one part or less per million detection of the gas.

24. The means of claim 21, wherein the equipment is an electrical device.

25. The means of claim 21, wherein the equipment is a means for processing air.

26. The means of claim 21, wherein the equipment is an internal combustion mechanism.

27. The means of claim 21, wherein the equipment is an external combustion mechanism.

28. The means of claim 27, wherein the external combustion mechanism may be a space heater, boiler or furnace.

29. A health monitoring system comprising:
    micro gas detector connected to an equipment so as to detect a gas from the equipment; and
    a processor connected to said micro gas detector; and wherein:
    the micro gas detector comprises:
        a channel for a flow of a fluid from the equipment;
        at least two interactive elements situated along a length of the channel; and
        at least two heater elements thermally connected to a corresponding interactive element of the at least two interactive elements; and
    the processor is connected to the at least two heater elements to energize the heater elements in a time phased sequence and provide an increased heat pulse for a fluid from the equipment as the fluid moves through the channel.

30. The system of claim 29, wherein said micro gas detector and processor may detect and identify, respectively, a gas of the ambient air that indicates the health of ambient air.

31. The system of claim 30, wherein said micro gas detector and processor may detect and identify, respectively, a gas of the ambient air that indicates a level of toxins-to-people in the ambient air.

32. The system of claim 30, wherein said micro gas detector may do one part or less per million detection of the gas.

33. The system of claim 32, wherein the gas may of a group including pollutants such as aldehydes, butyric acid, toluene, hexane, carbon dioxide, carbon monoxide and water vapor.

34. The system of claim 29, wherein;
    said micro gas detector may detect a fault gas from the equipment; and
    said processor may identify the detected fault gas and thus provide an early indication of decreased performance or failure of the equipment.

35. The system of claim 34, further comprising a communications link from said processor to an observing station.

36. The system of claim 35, wherein the equipment is an electrical device.

* * * * *